US006632428B1

(12) United States Patent
Zhang et al.

(10) Patent No.: US 6,632,428 B1
(45) Date of Patent: Oct. 14, 2003

(54) METHODS AND COMPOSITIONS EMPLOYING RED RICE FERMENTATION PRODUCTS

(75) Inventors: Mao Liang Zhang, Beijing (CN); Chi-Xiu Peng, Beijing (CN); Yu-Fang Zhou, Beijing (CN)

(73) Assignee: Peking University, Bejing (CN)

( * ) Notice: Subject to any disclaimer, the term of this patent is extended or adjusted under 35 U.S.C. 154(b) by 0 days.

(21) Appl. No.: 09/542,438

(22) Filed: Apr. 4, 2000

Related U.S. Application Data

(60) Division of application No. 08/965,202, filed on Nov. 6, 1997, now Pat. No. 6,046,022, which is a continuation-in-part of application No. 08/720,548, filed on Sep. 30, 1996, now abandoned.

(51) Int. Cl.[7] .................. A01N 63/04; A61K 35/72; A61K 35/78; C12P 1/02
(52) U.S. Cl. .................. 424/93.51; 424/195.16; 424/725; 424/750; 424/780; 435/41
(58) Field of Search .................. 424/93.51, 195.16, 424/725, 750, 780; 435/41

(56) References Cited

U.S. PATENT DOCUMENTS

| | | | |
|---|---|---|---|
| 3,983,140 A | 9/1976 | Endo et al. | 260/343.5 |
| 4,031,250 A | 6/1977 | Haas et al. | 426/18 |
| 4,049,495 A | 9/1977 | Endo et al. | 195/36 |
| 4,137,322 A | 1/1979 | Endo et al. | 424/273 |
| 4,231,938 A | 11/1980 | Monaghan et al. | 260/343.5 |
| 4,294,846 A | 10/1981 | Albers-Schonberg et al. | 424/279 |
| 4,294,926 A | 10/1981 | Monaghan et al. | 435/125 |
| 4,319,039 A | 3/1982 | Albers-Schonberg et al. | 560/256 |
| 4,342,767 A | 8/1982 | Albers-Schonberg et al. | 424/250 |
| 4,420,491 A | 12/1983 | Albers-Schonberg et al. | 424/311 |
| 5,362,638 A | 11/1994 | Dahiya | 435/125 |
| 5,627,068 A | 5/1997 | Kujumdzieva et al. | 435/254.1 |
| 5,712,130 A | 1/1998 | Hajko et al. | 435/123 |

FOREIGN PATENT DOCUMENTS

| | | |
|---|---|---|
| CN | 1075875 A | 9/1993 |
| CN | 1106230 A | 8/1995 |
| CN | 1110560 A | 10/1995 |
| CN | 1155421 A | 7/1997 |
| CN | 1173361 A | 2/1998 |
| DE | 3006216 | 2/1980 |
| DE | 3051175 | 2/1980 |
| GB | 2046737 | 2/1980 |
| GB | 2055100 | 7/1980 |
| JP | 55-150898 | 11/1980 |
| JP | 58-43783 A | 3/1983 |
| JP | 62-132878 A | 6/1987 |
| JP | 63-198973 A | 8/1988 |

OTHER PUBLICATIONS

Yan et al., "Effects of Xuezhikang on blood lipids and lipoprotein concentrations of rabbits and quails with hyperlipideaemia", Chinese Pharmaceutical Journal, vol. 30, No. 11, pp. 656–660, 11/95.
Han, Mei et al., "Experimental Study on the Decholesterolization of Metabolites from Monascus Rubber", Microbiology, vol. 21, No. 5, 10/94, pp.
Read, B.E., 1936, Chinese Medicinal Plants from the Pen Ts'ao Kang Mu, 3rd edition, published by Peking National History Bulletin.
Klein, G., 1932, Handbuch der Pflanzenanalyse II, 1422–1423, Wien Verlag von Julisu Springer.
"Tien Kun'ai Wu–chinese technology in the seventeenth century", translated by E–tu Zen Sun and Shiou–Chuan Sun, The Pennsylvania State University Press pp. 291–294, 1966.
Fielding et al.,1961, J. Chem. Soc., 4579–4589.
Broder et al., 1980, J. Food Sci. 45:567–469.
Wong, 1977, Plant Physiol, 60:578–581.
Grundy, New Eng. J. Med., 1988, 319:24–33.
Endo et al., J. Antibiotics, 1975, 29:1346–1348.
Tsujita et al., Atherosclerosis, 1979, 32:307–313.
Endo, J. Antibiotics, 1979, 32:852–854.
Endo, J. Antibiotics, 1980, 33:334–336.
Tobert et al., J. Clin Invest, 1982, 69:913919.
Tobert, Am J. Cardiol, 62:28J–34J.
The Merck Manual, 1992, 16th edition, pp. 1044–1046.
Pi–Sunyer, Am J. Clin Nutr., 1991, 53:1595S–1603S.
Feling et al., 1975, N. Eng. J. Med. 293:1078–1084.

*Primary Examiner*—Jon P. Weber
*Assistant Examiner*—Kailash C. Srivastava
(74) *Attorney, Agent, or Firm*—Fish & Richardson P.C.

(57) ABSTRACT

Methods and compositions are disclosed which comprise red rice fermentation products, that can be used as natural dietary supplements and/or medicaments for the treatment or prevention of hyperlipidemia and associated disorders and symptoms, such as cardiovascular diseases, cerebrovascular diseases, diabetes, hypertension, obesity, asthenic breathing, chronic headache, chest pain and tightness, limb swelling and distention, loss of appetite and excess expectoration. The methods and compositions are effective in lowering both the serum cholesterol and serum triglyceride levels in humans, and can be used for maintaining cardiovascular health. The invention also encompasses particular Monascus strains that yield fermentation products with the desired biological activities.

3 Claims, No Drawings

METHODS AND COMPOSITIONS EMPLOYING RED RICE FERMENTATION PRODUCTS

CROSS-REFERENCE TO RELATED APPLICATIONS

This Application is a Divisional of U.S. Ser. No. 08/965,202, filed Nov. 06, 1997, now U.S. Pat. No. 6,046,022, which is a CIP of U.S. Ser. No. 08/720,548, filed Sep. 30, 1996, now abandoned, incorporated herein by reference in full.

FIELD OF THE INVENTION

The invention relates to the fields of rice fermentation and treatment of hyperlipidemia. More particularly, the invention relates to red rice fermentation products and methods, and use of the products to treat high cholesterol levels and other disorders.

BACKGROUND OF THE INVENTION

The invention relates to compositions comprising red rice fermentation products, that can be used as dietary supplements and/or therapeutic medicaments. For example, the compositions can be used to lower serum cholesterol and triglycerides in mammals. Further, the invention relates to methods of treating cardiovascular disorders and other diseases using the red rice fermentation products. In addition, the invention relates to particular Monascus strains that yield fermentation products with the desired biological activities.

Red Rice in Ancient China

Red rice is known mostly for its use in food as a preservative and colorant, and its uses in the dye industry. Red rice (known in Chinese as Hung-ch'u or Hongqu) has also been known and used for hundreds of years in China in rice wine making and as a food preservative. In addition, red rice has been known as an ancient Chinese medicine or an ingredient in certain ancient Chinese prescriptions.

Red Rice was first used around the time of the Han Dynasty. Tao Gu, who lived in the age of Wudai after the Tang Dynasty, recorded "Red Yeast Rice Cooked with Meat," in Qing Yi Lu. The method of making Red Rice was originally recorded in Tien Kyng K'ai Wu and Pen Ts'ao Kang Wu, A detailed description of the medical applications of red rice was provided in the ancient Chinese pharmacopoeia, Pen Ts'ao Kang Mu, which was published during the Ming dynasty (1368–1644). In Pen Ts'ao Kang Mu, Red Rice is described as mild, nonpoisonous, and useful for treating indigestion and diarrhea. Red Rice is also described as useful for improving blood circulation and promoting the health of the spleen and stomach. Furthermore, several "prescriptions" using red rice for treating aliments, such as indigestion, diarrhea, and heart and abdominal pains, are also provided in this ancient work. In accordance with the Traditional Chinese Medicine Standard set forth in Pharmacopoeia of People's Republic of China and the Traditional Chinese Medicine standard of Beijing, Nei Monggol, Shadog Provice, Jiangsu Province and Hunan province, etc., Red Rice is specified to be used as a traditional Chinese medicine. Furthermore, in the textbooks of Chinese universities and colleges such as Food Additives and Food Chemistry, Red Rice is considered as additives for food and beverages, and has been widely used in the food processing industry for the production of such items as fermented bean curd, beer, and meat.

In an abbreviated English translation of Pen Ts'ao Kang Mu published in 1911, red rice is described as useful for fermentation, and having medicinal value in the treatment of postpartum difficulties in women and dyspeptic conditions of children (Stuart, M. D., in "Chinese Materia Medica—Vegetable Kingdom," page 233–234, republished in 1979 by Southern Materials Center, Inc., Taipei, Republic of China). Red rice, as described in Pen Ts'ao Kang Mu, was subsequently recognized to be the fungal species known as *Monascus purpureus* Went (Read, B. E., 1936, Chinese Medicinal Plants from the Pen Ts'ao Kang Mu, 3rd edition, published by Peking National History Bulletin; Klein, G., 1932, Handbuch der Pflanzenanalyse II, p. 1422–1423, Wien, Verlag von Julius Springer).

The manufacture of red rice is taught in another publication from the Ming dynasty, Tien Kung K'ai Wu by Sung Ying-Hsing, which was published in 1637 A.D. (see pages 291–294 in English translation of this ancient writing, "Tien Kung K'ai Wu—Chinese technology in the seventeenth century," translated by E-tu Zen Sun and Shiou-Chuan Sun. The Pennsylvania State University Press 1966). Red rice is described therein as useful for preserving the color and taste of fish or meat. The manufacturing process used red wine mash and cooked nonglutinous rice as starting materials. The method of making red rice by allowing the fungus to grow on the surface of cooked rice was also recorded by Voderman (1894. Analecta ob Cromatologisch Gebied. II. Geneesh. Fylschrift voor Ned. Indie, 35, No.5).

Modernly, red rice, the fermentation product of Monascus species, is still used in traditional Chinese medicine, wine making and food coloring in Asia and Asian communities in North America. The red and yellow pigments of *Monascus purpureus*, such as monascorubin and monascin, have been purified and extensively studied (Fielding et al., 1961, *J Chem Soc*, 4579–4589). The culture conditions and its effect on pigmentation of *Monascus purpureus* have also been studied (Broder et ad., 1980, *J Food Sci*, 45:567–469). Antibacterial activity, especially against Bacillus species, was also detected in *Monascus purpureus* extract (Wong, 1977, *Plant Physiol*, 60:578–581). The Red Rice of the traditional methods has been shown to be of little value and thus has gradually fallen out of use in medical applications. The traditional Red Rice has little effect of reducing blood lipids, and thus has never been used as a cholesterol lowering agent.

Hyperlipidemia and Dietary/Medical Intervention

Lipids and lipoproteins play an essential role in transporting fat-derived metabolites between organs for absorption, metabolism, and distribution (Felig et al., 1975, *N Eng J Med*, 293:1078–1084). The susceptibility to dietary-induced elevations in blood lipids including cholesterol is extremely common. The interaction of genetic predisposition and a high fat, high caloric diet coupled with underactivity can lead to heart disease, hypertension, hypertriglyceridemia, and diabetes in a significant proportion of the United States population.

High serum cholesterol is a major risk factor for coronary artery disease. Cholesterol is a major component of atherosclerotic plaque. Other associated lipid abnormalities, including hypertriglyceridemia especially in the presence of lowered HDL cholesterol levels, have been recognized as contributing to the risk of cardiovascular disease. There is a reciprocal relationship between elevated triglyceride levels and lowered HDL levels.

The level of cholesterol in circulation results from the balance between production of apoB-100 particles and its removal from the circulation. Cholesterol is synthesized from acetyl-CoA via a series of more than 20 enzymatic reactions. This biosynthetic pathway is mainly regulated by the activity of HMG-CoA reductase (hydroxymethylglutaryl coenzyme A reductase), which catalyzes the reduction of HMG-CoA to mevalonate. Since the majority of cholesterol circulating is endogenously synthesized in the liver, and not derived from dietary cholesterol, inhibitors of enzymes that are involved in the biosynthesis of cholesterol have been explored as drugs for the treatment of hypercholesterolemia (Grundy, *New Eng J Med* (1988) 319:24–33).

One class of compounds inhibits cholesterol biosynthesis by competing with a natural substrate (HMG-CoA) for the key enzyme in the cholesterol biosynthetic pathway, HMG-CoA reductase. The first such hypocholesterolemic compound discovered was compactin, which was isolated from cultures of *Penicillium citrinum* by Akira Endo (Endo et al., *J Antibiotics* (1975) 29:1346–1348, see also U.S. Pat. Nos. 3,983,140, 4,049,495, and 4,137,322). The hypocholesterolemic activity of this compound was demonstrated in several animal species (Tsujita et al., *Atherosclerosis* (1979) 32:307–313). Thereafter, a hypocholesterolemic compound structurally related to compactin was independently discovered by Endo in fermentation products of *Monascus ruber* (the active compound was named monacolin K; Endo, *J Antibiotics* (1979) 32:852–854; Endo, *J Antibiotics* (1980) 33:334–336; see also German patents DE 3051175, 3051099 and 3006216; British patents GB 2046737 and 2055100), and by another group from cultures of *Aspergillus terreus*. The active compound was also named mevinolin, lovastatin or Mevacor®; Tobert et al., *J Clin Invest* (1982) 69:913–919), and has been available in the United States since 1987 as a prescription drug. The efficacy and long term adverse effect of this active compound has been reviewed (Tobert, *Am J Cardiol*, 62:28J–34J). The isolated active compound, its derivatives and methods of production from Aspergillus have been reported; see U.S. Pat. Nos. 4,231,938, 4,342,767, 4,294,926, 4,319,039, 4,294,926, 4,294,846, and 4,420,491.

Although monacolin K or mevinolin has been successfully used to treat hypercholesterolemia, the compound has little or insignificant effect on the serum level of triglycerides. Other lipid regulating agents that have been used to treat hypertriglyceridemia, especially type IV and V hyperlipidemia, include nicotinic acid (e.g., niacin), and fibric acid derivatives (e.g., gemfibrozil and clofibrate). However, the uses of such agents are restricted because of their side effects, for example, high doses of niacin may cause gastric irritability, hyperuricemia hyperglycemia, pruritus, and gemfibrozil may lead to malignancy, gallbladder diseases, and abdominal pain. Moreover, the risk of myositis and rhabdomyolysis that can result in renal failure increases when monacolin K is combined with gemfibrozil, clofibrate or niacin. Such combinations are only used with careful supervision in special situations that warrant the risk (The Merck Manual, 1992, 16th edition, pages 1044–1046). High concentrations of serum triglycerides are known to be a risk factor for a variety of disease states and can lead to medical complications. Thus, there is a need for the development of a composition that accomplishes the reduction of the serum levels of both cholesterol as well as triglycerides. Regular exercise, proper nutrition, and weight reduction programs can prevent or reduce the incidence of common chronic diseases such as heart disease associated with elevations of blood lipids (Pi-Sunyer, *Am J Clin Nutr* (1991) 53:1595S–1603S). The role of diet in maintaining optimal health, and in slowing and reversing the progression of disease, has been the subject of much research and public attention. The development of an effective dietary supplement for use in the treatment of mixed hyperlipidemia, which could be used either with or without dietary changes, would be a significant benefit.

SUMMARY OF THE INVENTION

The invention relates to a product of the fermentation of at least one Monascus strain that can be used as a dietary supplement or as a therapeutic medicament to lower both serum cholesterol and triglyceride levels in humans. The invention is based, in part, on the surprising discovery that certain red rice products, i.e., the product of the fermentation of certain strains or mixtures of strains of Monascus, are effective at lowering not only the level of serum cholesterol but also the level of serum triglyceride in mammals, particularly humans. Since monacolin K and mevinolin are not known to be significantly effective in lowering serum triglyceride level, the beneficial effect of red rice products is likely to be related to other components in the fermentate.

In various embodiments of the invention, red rice can be used as a natural dietary supplement or a medicament to treat or prevent a variety of diseases, including but not limited to cardiovascular diseases, diabetes, fatty liver conditions, stroke, cerebral thrombosis, hypotension, hypertension and obesity, and to modulate the circulating levels of lipids, such as cholesterol and triglyceride. In addition, the present invention encompasses methods for treating or preventing these diseases in a human, which comprise administering to the human a therapeutically effective amount of a red rice fermentation product. The present invention also encompasses methods for improving or maintaining cardiovascular health in a human comprising administering to an effective amount of red rice fermentation product. The present invention further encompasses methods for reducing the serum cholesterol and serum triglyceride levels to normal levels in a human comprising administering to the human a therapeutically effective amount of a red rice fermentation product. Red rice can also be used to treat or prevent a variety of ailments or symptoms as related to diseases of the cardiovascular system.

According to the invention, red rice can be manufactured in various dosage forms and formulations. Also disclosed are methods for manufacturing red rice which are based on the traditional fermentation procedures.

The terms "red rice fungi" or "Monascus" as used herein refer to the prefermented organism, while the terms "red rice," "red rice product", "red rice extract" and the like refer to a product that results from the fermentation of at least one Monascus. Further, these latter terms include traditional and improved red rice products as described below. More specifically, "red rice product" as used herein refers to the product of fermentation, e.g., the fermentate of one or a mixture of Monascus fungus. A "lovastatin-producing" Monascus strain (such as strain 0272) is one which can be fermented to produce a product having a lovastatin content of at least 0.05%, preferably at least 2%.

The red rice product is the fermentation product of at least one of the following Monascus fungi set forth in the table below Red rice is the fermentation product of one or a mixture of Monascus fungi, comprising chiefly *Monascus purpureus* Went, and in lesser proportions other Monascus species, e.g., *Monascus ruber* van Tieghem, *Monascus Fuliginosus* Sato,

*Monascus Pilosus* Sato and *Monascus albidus* Sato. Red rice can also be the fermentation product of the following strains of Monascus fungi:

| Strains | Accession No. |
| --- | --- |
| *Monascus albidus* Sato | AS 3.570 |
|  | AS 3.4440 |
|  | CGMCC No. 0317 |
| *Monasuc pilosus* Sato | AS 3.4444 |
|  | AS 3.4633 |
|  | AS 3.4646 |
|  | AS 3.4647 |
| *Monascus pubigerus* Sato | AS 3.4445 |
| *Monascus ruber* van Tieghem | AS 3.549 |
|  | CGMCC No. 0315 |
|  | CGMCC No. 0316 |
| *Monascus paxii* Lingelsheim | AS 3.4453 |
| *Monascus fuliginosus* Sato | AS 3.569 |
|  | AS 3.1098 |
|  | AS 3.2091 |
|  | AS 3.2093 |
|  | AS 3.2134 |
|  | IFFI 05035 |
| *Monascus purpureus* Went | CGMCC No. 0272 |

*Monascus purpureus* Went ATCC 30141, AS 3.562, AS 3.991, AS 3.4446 [ATCC 16365], AS 3.4642 [NRRL 2897], AS 3.4643 [NRRL 96], AS 3.4644, AS 3.4645, AS 3.4651; *Monascus ruber* van Tieghem AS 3.549, IFFI 05007, IFFI 05008, IFFI 05010, IPPI 05011; and *Monascus anka* IFFI 05038 (reference numbers provided in China Catalogue of Cultures, 1992, China Committee for Culture Collection of Microorganism, China Machine Press, Beijing 1992). The improved red rice of the invention comprises *Monascus purpureus* Went mutant strain M4027, 4028 and M4184.

The term "traditional red rice" as used herein refers to a red rice product which is the result of fermentation using a mixture of Monascus fungi that has been used traditionally to manufacture red rice. "Traditional red rice" will generally contain less than about 0.005% lovastatin by weight. According to the invention, an "improved red rice" is produced by fermentation using one or more natural or mutant strains of Monascus species, which yield a fermentate with improved biological or nutritional properties, e.g., higher hypocholesterolemic and hypotriglyceridemic activities than traditional red rice. The improved red rice of the invention comprises *Monascus purpureus* Went mutant strain CGMCC No. 0272. Several other strains can be used to achieve the objectives of the invention. Improved red rice is sometimes referred to as Xuezhikang herein.

Generally, the red rice products of the present invention are red-purple powders that have a slightly bitter but mild and pleasant taste. Similarly, the red rice products have a pleasant odor. The color and/or odor may vary with the fermentation process, the strains used and the processing steps. The red rice products of the invention contain at least 0.05% lovastatin, more preferably at least about 2.0% lovastatin by weight.

As used herein, the term "effective treatment" means the reduction of a particular symptom, or the significant change of a particular laboratory test toward the normal value. Preferably symptoms are relieved by at least 30–70% and a laboratory test is moved at least 10% toward the normal value; more preferably symptoms are reduced by 70% and/or a laboratory test is moved at least 20% toward the normal value; most preferably, a treatment is effective if the symptoms are reduced by 90%, and/or laboratory parameters are returned to the normal value.

The term "hypercholesterolemia" means the presence of elevated levels of cholesterol in the blood.

The term "therapeutically effective amount" or "therapeutic dose" as used herein means the amount of a particular agent sufficient to provide a therapeutic benefit in the treatment or prevention of a disease, or in modulating the level of serum lipids and lipoproteins.

The term "dietary supplement" as used herein means an additional element that is added to the daily food intake of a mammal, usually a human.

Unless otherwise defined, all technical and scientific terms used herein have the same meaning as commonly understood by one of ordinary skill in the art to which this invention belongs. Although methods and material similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

DETAILED DESCRIPTION OF THE INVENTION

The invention relates to compositions comprising the product of the fermentation of at least one Monascus species. These compositions are useful for reducing the levels of both serum cholesterol and serum triglycerides in mammals, and in particular humans. In addition, the compositions are useful for modulating the levels of both serum cholesterol and triglycerides to maintain healthy levels despite intrinsic (e.g. aging) or extrinsic (e.g. stress) factors that affect serum cholesterol and triglyceride levels. The compositions and methods of the present invention are based, in part, on the discovery that the fermentate of Monascus species display hypocholesterolemic properties and also, unexpectedly, the ability to lower serum triglyceride levels. Since monacolin K is known not to be significantly effective in lowering serum triglyceride level, the beneficial effect of red rice products must be related to other components of the fermentate. The ability of red rice products to lower serum triglyceride level provides the art with a unique, natural alternative to the use of prescription hypocholesterolemic compounds.

According to the invention, traditional or improved red rice can be prepared by traditional fermentation procedures or by modification of the traditional procedures. According to the earliest reported method (Sung, 1637, Tien Kung K'ai Wu; pages 291–294, English translation by Sun et al., Pennsylvania State Press 1966), red rice can be prepared by the fermentation of washed and cooked nonglutinous rice using red wine mash, natural juice of Polygonum grass, and alum water. The rice is fermented in open air for 7 days on bamboo trays under very clean conditions. The rice changes its color from white to black, black to brown, brown to red and then red to yellow, which is then harvested as red rice. According to an alternative traditional method, nonglutinous rice can be fermented in a hole in the ground lined by bamboo mats, which is securely covered. Fermentation is allowed to take place underground for one year or more, up to four years.

With respect to the present invention, the traditional method has been improved by use of modem fermentation techniques and equipment to more precisely control temperature, pH, pressure and other fermentation parameters, which, inter alia, reduces the time of fermentation. The key feature of the improved red rice preparation is that it contains active ingredients that can prevent or treat hyperlipidemia and related cardiovascular diseases. The preparations can be made as follows:

Preparation of Conventional Culture Fluid

For all of the media preparations rice or another grain is used as a carbon source. The carbon source can be rice (polished long-grain nonglutinous rice, polished round-grain nonglutinous rice, polished glutinous rice, red rice, and black rice), millet, barley, wheat, or corn. Additionally sugar and substances containing sugar can be used. Organic compounds such as glycerine and glyceride can also be used in the media preparations. For each 100 g of polished round-grained nonglutinous rice, 30–80 ml of culture medium are added. The culture media's key feature is that the carbon source is selected from the group consisting of cereals, sugar, and organic compounds, the source of nitrogen is selected form the group consisting of beans (e.g. soya bean powder, pressed soybean cake), or peanut powder (or pressed peanut cake), peptone, rice extract powder, thick beef juice, silkworm chrysalis powder, or inorganic salts (e.g. $NH_4NO_3$, etc.), and a source of phosphorous can also be added, such as inorganic salts (e.g. $KH_2PO_4$, $K_2HPO_4$, etc). Other inorganic salts can also be added, such as $MgSO_4$ or $FeCl_2$. By way of an example, and not by limitation, media preparations of the invention are listed below:

Media 1: Liquid Strain

2–7% glycerine (or malt or potato juice)

26% sugar

0–3% peptone 0.5–3% yeast extract powder

0–3% thick beef juice (optional)

2–4% defoamer (e.g. bean oil or peanut oil) water

Media 2: Solid Strain

0–5% Potato juice

0–6% sugar

0–1.5% yeast extract or peptone

30–80 ml of water per 100 g rice

Media 3

2–4% potato juice

2–6% sugar 0.5–3% yeast extract powder (or peptone or thick beef juice) water.

Approximately 40–80 ml of the mixture is added to each 100 g of rice, the pH is maintained at 3–8, and it is sterilized in steam at 121° C.

Generally, the pH is adjusted to 3.0–5.0, and the mixture is steam sterilized (121° C.). The mixture is cooled to 40° C. and the rice is inoculated with the a Monascus strain of the invention. For example, the *Monascus purpureus* Went strain CGMCC No. 0272 is added and cultured at 15–35° C. for 9 days. Fermentation of the rice mixture is preferably carried out at a temperature of 15–35° C., most preferably 20–28° C., for over 4 days, most preferably 9 days or more, until the formation of Red Rice is noted. Any one of a number of methods of fermentation, well known to one of skill in the art, can be used. For example, an Erlenmeyer flask, tray, or ventilated fermentation bed can be used as fermentation facilities. At the end of the fermentation process, the fermentation broth is drained and discarded, while the solid residue is sterilized by heat (for example, by high pressure steam). For example, the fermentation product is sterilized at a temperature of 69–121° C., and dried. This dried product can be ground. Standard mesh sizes for the production of capsules, tablets, powders and suspensions are well known in the art. By way of example, the improved red rice of the invention can be ground to 80 mesh under vacuum at a temperature of approximately 60–80° C., and the powdered product recovered. This product can be used directly in the various compositions and formulations provided by the present invention. For example, it can be filled into capsules. Alternatively the 80 mesh ground product can further be ground to 200 mesh. The 200 mesh powder can then formulated into tablets using standard methodologies. Alternatively, liquid or syrup formulations of red rice can be made using conventional procedures.

Optionally, the dried crushed red rice powder can be further processed, e.g., extracted with organic solvents, such as but not limited to, alcohols (e.g. 75–90% ethanol) to remove starch and/or agar. After evaporation to dryness, the extract can be used in the various compositions and formulations as provided by the present invention. The extracted product can further be concentrated under a vacuum and evaporated (60–80° C., 0.06–0.08 MPa) until dry. This provides an exceptionally useful supplement at very low cost.

According to the invention, an "improved red rice" is produced by fermentation using one or more natural or mutant strains of Monascus species, which yield a fermentate with improved biological or nutritional properties, e.g., higher hypocholesterolemic and hypotriglyceridemic activities than traditional red rice. The improved red rice of the invention comprises *Monascus purpureus* Went mutant strain M4027, 4028 and M4184. Several other strains can be used to achieve the objectives of the invention (Chinese Microorganism Strain Index, 1992, China Microorganism Collection Committee), as listed in the Table above.

Lovastatin in red rice may be extracted using 10 ml of 75% EtOH at ambient temperature. The extract (2 ml) is treated with 1 ml 0.06 M NaOH in 75% EtOH for 30 min, then with 1 ml 0.06 N $H_3PO_4$ (in 75% EtOH, and the mixture applied to a C18 HPLC column (150×4.60 mm), and developed with 0.02 N $H_3PO_4$ (in 70% MeOH) to quantify the amount of lovastatin present.

Red rice can be used as a natural dietary supplement or a pharmaceutical medicament to prevent illness (maintain health) or to treat or a variety of diseases, including but not limited to cardiovascular diseases, diabetes, stroke, hypertension and obesity, and to modulate the circulating levels of lipids and lipoproteins, such as cholesterol and triglycerides. Red rice can also be used to treat or prevent a variety of symptoms related to these above-mentioned diseases and associated with poor cardiovascular health due to aging and other intrinsic and extrinsic factors.

As used herein, examples of cardiovascular diseases may include but are not limited to myocardial infarction, coronary heart disease, atherosclerosis, arteriosclerosis. The present invention includes the treatment or prevention of cerebrovascular disease such as stroke, memory loss due to stroke, and cerebral thrombosis.

The present invention also encompasses a composition comprising a therapeutically effective amount of a red rice product, for example 2–4 grams per day, useful in humans for the treatment or prevention of hyperlipidemic disease, cardiovascular disease, cerebrovascular disease, hypertension, hypotension, diabetes, fatty liver conditions, or obesity, or a combination thereof.

The present invention further encompasses a composition comprising a therapeutically effective amount of a red rice product, useful for the modulation of serum lipid and lipoprotein levels in a human in need of therapy to maintain the lipid and lipoprotein levels within a healthy normal range. In one embodiment of the invention, the composition is adapted for use in the treatment or prevention of hypertriglyceridemia. In a preferred embodiment, such a composition is used for reducing serum cholesterol and serum triglyceride levels in humans.

The present invention further encompasses a composition comprising a therapeutically effective amount of improved red rice product, useful for the treatment of any one of the following symptoms: shortness of breath; asthenic breathing; lethargy; dizziness; chronic headache; chest pain and tightness; heartache; loss of appetite; limb swelling; tightness and distention.

Functions of Improved Red Rice

The improved red rice of the invention and preparations of the improved red rice contain statinoid compounds, i.e. hydroxy-acid Lovastatin and lactone Lovastatin.

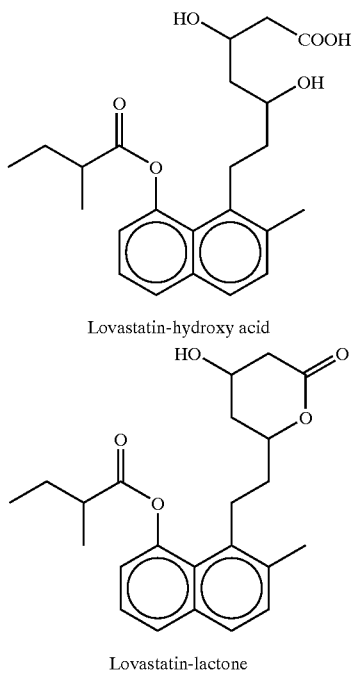

Lovastatin-hydroxy acid

Lovastatin-lactone

Without being bound by theory, the above-mentioned Monascus strains, when cultured under the appropriate fermentation conditions, have an increased content of the statinoid compounds. The increase in the statinoid compounds reduces serum cholesterol and serum triglycerides, while increasing high-density lipoprotein cholesterol simultaneously.

The red rice of the invention can be employed to treat hyperlipidemia and other related cardio-cerebrovascular diseases, such as atherosclerosis, coronary heart disease, myocardial infarction, diabetes, hypertension, and cerebral embolism, among others.

Method of Treatment

The present invention provides methods for treating a human afflicted by a variety of diseases, disorders, and symptoms. In addition to treatment of a human disease, the methods of the invention can also be used for preventive treatment in a person susceptible to such diseases, disorders or symptoms.

The invention encompasses methods of treatment of hyperlipidemic disease, cardiovascular disease, cerebrovascular disease, hypertension (hereditary and non-hereditary), hypotension, angina, stroke, diabetes, fatty liver conditions, or obesity, or a combination thereof in a human, comprising administering to the human a therapeutically effective amount of a red rice product, or compositions containing said product.

The invention also encompasses methods of preventing hyperlipidemic disease, cardiovascular disease, cerebrovascular disease, hypertension, hypotension, angina, stroke, diabetes, fatty liver conditions such as fatty liver deposits, obesity or a combination thereof, which comprises administering an effective amount of a red rice product of the present invention. The method of the invention is preferably used to treat or prevent hypertriglyceridemia and associated diseases, such as diabetes, in humans.

As used herein, examples of cardiovascular diseases may include myocardial infarction, coronary heart disease, atherosclerosis, arteriosclerosis, and cerebrovascular diseases or conditions, including stroke, cerebral thrombosis or memory loss due to stroke.

The present invention also provides methods for modulating serum lipid and lipoprotein levels in a human in need of lowering the lipid and lipoprotein levels to a healthy normal range, which comprise administering to the human a therapeutically effective amount of a red rice product, or compositions containing said product. In a preferred embodiment, the method of the invention is used to reduce serum cholesterol and serum triglyceride levels in a human. The methods of the invention are particularly useful for the treatment of geriatric patients and postmenopausal women.

The present invention further provides methods for treating a human afflicted by shortness of breath, asthenic breathing, lethargy, dizziness, chronic headache, loss of appetite, limb swelling, tightness and distention, and abdominal distention, or a combination thereof, which comprises administering to the human a therapeutically effective amount of a red rice product, or compositions containing said product.

The preventive or therapeutic dose of traditional red rice or improved red rice in the treatment or prevention of diseases and in the management of serum lipid and lipoprotein levels will vary with the condition to be treated and the severity of the condition to be treated. The dose, and perhaps the dose frequency, will also vary according to the age, body weight, and response of the individual patient. In general, the total daily dose range of red rice, for the conditions described herein, is from about 0.1 g to about 5 g administered in single or divided doses orally. For examples a preferred oral daily dose range should be from about 0.3 g to about 4 g, while most preferably an oral daily dose should be about 1.2 to about 2.5 g. For example, two capsules each containing 0.6 g of red rice may be taken orally twice a day to obtain the preferred dose. A course of treatment should be at least 4 weeks. It may be necessary to use dosages outside these ranges in some cases as will be apparent to those skilled in the art. Further, it is noted that the nutritionist, dietitian, clinician or treating physician will know how and when to interrupt, adjust, or terminate therapy in conjunction with individual patient response.

It should be noted that the present invention encompasses new uses of traditional red rice, and novel red rice products and novel methods of using those products.

Dietary Supplement Use

As mentioned above, the present invention encompasses compositions and methods of using traditional and novel or improved red rice products as dietary supplements. As such, the red rice products provide the individual with a means for maintaining normal or healthy levels of serum cholesterol and triglycerides despite intrinsic deterioration, e.g., from aging and extrinsic factors such as stress, lack or exercise and poor nutrition. The dietary supplements also provide means for preventing, or reducing the likelihood or experiencing, the diseases discussed above. Finally, the dietary supplements can be used to prevent weight gain or obesity. Finally, the dietary supplements containing red rice products are particularly useful for the elderly and post-menopausal women. The dietary supplements should be taken daily for at least four weeks and can be used permanently on a daily basis. A daily dose is from about 0.1 g to about 5.0 g; preferably about 1 to about 4 g; and most preferably about 1.2 to about 2.4 grams per day.

Formulation

The pharmaceutical and dietary compositions of the present invention comprise a red rice product, or an extract thereof, as active ingredient, and may also contain a pharmaceutically acceptable carrier or excipient and, optionally, other ingredients.

Other ingredients that can be incorporated into the dietary or pharmaceutical compositions of the present invention may include, but are not limited to, vitamins, amino acids, metal salts and flavor enhancers. For oral administration, the compositions comprising red rice can be added directly to foods so that a therapeutically effective amount of red rice is ingested during normal meals. Any methods known to those skilled in the art may be used to add or incorporate red rice to natural or processed foods.

Compositions of the present invention suitable for oral administration may be presented as discrete units such as capsules, cachets, or tablets, each containing a predetermined amount of a red rice product, as a powder or granules, or as a solution or a suspension in an aqueous liquid, a nonaqueous liquid, an oil-in-water emulsion, or a water-in-oil liquid emulsion. In general, the compositions are prepared by uniformly and intimately admixing the active ingredient with liquid carriers or finely divided solid carriers or both, and then, if necessary, shaping the product into the desired presentation.

The compositions of the present invention may additionally include binding agents (e.g., pregelatinized maize starch, polyvinylpyrrolidone or hydroxypropyl methylcellulose); binders or fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets or capsules can be coated by methods well known in the art.

Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats), emulsifying agents (e.g., lecithin or acacia), nonaqueous vehicles (e.g., almond oil, oily esters, ethyl alcohol or fractionated vegetable oils), and preservatives (e.g., methyl or propyl-p-hydroxybenzoates or sorbic acid). The preparations can also be made to resemble foods, containing buffer salts, flavoring, coloring and sweetening agents as appropriate.

Any dosage form may be employed for providing the patient with an effective dosage of the red rice product. Dosage forms include tablets, capsules, dispersions, suspensions, solutions, capsules and the like. Because of their ease of administration, tablets and capsules represent the most advantageous oral dosage unit form, in which case solid pharmaceutical carriers as described above are employed. In addition to the common dosage forms set out above, the compounds of the present invention may also be administered by controlled release means. However, the most preferred oral solid preparations are capsules.

For example, a tablet may be prepared by compression or molding, optionally, with one more accessory ingredients. Compressed tablets may be prepared by compressing in a suitable machine red rice in a free-flowing form such as powder or granules, optionally mixed with a binder, lubricant, inert diluent, surface active or dispersing agent. Most preferably, the composition is a capsule containing 0.3 g of red rice in powder form.

The invention is further defined by reference to the following examples describing in detail the human clinical trials conducted to study the efficacy and safety of red rice. It will be apparent to those skilled in the art that many modifications, both to materials and methods, may be practiced which are within the scope of this invention.

The invention will be further described in the following examples, which do are intended to provide further description of the invention, and are not intended to limit the scope of the claim.

EXAMPLE 1

Preparation of Red Rice Cultures (A) A liquid strain culture fluid was prepared containing 2–4% glucose, 3–5% glycerine, 0–3% thick beef juice, 0.8–1.6% peptone, 0–3% yeast extract powder, 0.1% $KH_2PO_4$, and 0.05% $MgSO_4 \cdot 7H_2O$ and water. Two media were prepared, the first containing 2% glucose, 3% glycerine, 1.5% thick beef juice, 0.8% peptone, 3% yeast extract powder, 0.1% $KH_2PO_4$, and 0.05% $MgSO_4 \cdot 7H_2O$ in water, and the second containing 4% malt juice or potato juice, 8% sugar, 1.5% yeast extract powder, 3% thick beef juice, and water. The pH was adjusted to 3.5 using acetic acid. For each 50 ml of culture fluid, 100 g of polished round-grained nonglutinous rice was added, and the media were sterilized in steam at 121° C. The mixture was cooled to below 40° C., and inoculated with *Monascus purpureus* Went (CGMCC No. 0272) in glass tubes or plates and cultured at 30–34° C. for 24–36 hours. Fermentation was continued at 25° C. for 9 days. Once the fermentation period was completed, the mixture was sterilized at high temperature (100–121° C.), dried under a vacuum at 80° C., and ground to 60–100 mesh. The powder was then filled into capsules. Yield approximately 65%.

(B) Alternatively, culture fluid containing 4% malt juice or potato juice, 8% glucose, 3% thick beef juice, 3% peptone and water (pH value adjusted to 3) was used. Following fermentation, the resulting product was extracted using 75–95% ethanol, the red rice was dried and fully mixed with untreated rice. Soya bean powder (10 g) and culture fluid (50 ml) were added to each 100 g mixture, and the composition was sterilized. The mixture was cooled to 30–40° C. and then inoculated with 10–20 ml liquid Monascus strain (CGMCC No. 0272), fermented at 30–34° C. for 34 days and at 23–25° C. for over 15 days.

The mixture was sterilized at 100–121° C. and dried under vacuum. This red rice product was ground and tablets were produced.

(C) Another medium was prepared using 4% malt juice, 6% malt sugar, 1% yeast extract powder, 6% peptone and water (pH=3). Soya-bean powder (15 g) and culture fluid (50 ml) was added to each 100 g of polished round-grained nonglutinous rice. The mixture was sterilized at 121° C. and then inoculated with Monascus ruber AS 3.549 (20 ml). Fermentation was carried out at 25° C. for over 9 days. After sterilization, the mixture was dried at 80° C.

The Red Rice was further processed into concentrates using alcohol (75%) extraction twice. After evaporation under vacuum, the concentrated substance was obtained and the alcohol was recovered. The resulting concentrated substance contained approximately 25 mg lovastatin per gram red rice, and was used as raw material for the production of the capsules or tablets.

(D) Another culture fluid was prepared containing 4% malt juice, approximately 8% sugar, 2% yeast extract powder, 5% thick beef juice and water (pH=3). Culture fluid (50 ml) was added to each 100 g of rice and the mixture was sterilized in steam at 121° C. After cooling below 40° C., the mixture was inoculated with *Monascus albidus* (CGMCC No. 0317) and then fermented at 25° C. for over 12 days. The mixture was sterilized and then dried. This Red Rice preparation was ground to 200 mesh and granulated with alcohol for pill preparation.

(E) Culture fluid was also prepared using 3% potato juice, approximately 6% sugar, 1.5% yeast extract powder, 4% peptone and water (pH=3). Soya bean powder (10 g) and culture fluid (80 ml) were added to each 100 g of rice and the mixture was sterilized in steam at 121° C. After cooling below 40° C., the mixture was inoculated with *Monascus pilosus* Sato (AS 3.4444), then cultured at 30–34° C. for 34 days, then cultured for over 10 days at 100–121° C. and then dried.

This Red Rice preparation was further processed into concentrates by using alcohol (75%) extraction. Small amounts of dissolvable starch were added for pill preparation.

(F) Culture fluid was also prepared using 3% potato juice, 5% sugar, 6% thick beef juice and water (pH=3). 10–20% peanut powder was added to culture fluid (80 ml) for each 100 g of rice, and the mixture was sterilized in steam at 121° C. After cooling below 40° C., the mixture was inoculated with *Monascus ruber* van Tieghem (CGMCC No. 0315) and then cultured at 30–34° C. for 3 days. The temperature was lowered to 24° C. and the culturing was continued for over 15 days. The mixture was sterilized in steam at 100–121° C. and dried.

(G) A medium was also prepared containing 3% corn juice or 3% potato juice, 6% sugar, 1.5% yeast extract powder, 4.5% peptone and water (pH=3). 5–20% of soya-bean cake powder and 80 ml of culture fluid were added to each 100 g of millet. The mixture was sterilized in steam at 121° C., cooled to a temperature below 40° C. inoculated with *Monascus pilosus* (AS 3.4633), and cultured at 25° C. for over 18 days. The mixture was sterilized at 121° C. and then dried under a vacuum at a temperature of 60–80° C.

(H) A medium was prepared containing 4% potato juice, 7% sugar, 8% peptone and water (pH=3). Culture fluid (60 ml) was added to each 100 g of rice, and the mixture was sterilized at 121° C. After cooling to a temperature below 40° C., the mixture was inoculated with *Monascus pubigerus* Sato (AS 3.4445), and then cultured at 30–34° C. for 3 days. The temperature was lowered to 25° C. and culturing was continued for over 9 days. The mixture was sterilized in steam at 121° C. and dried at 80° C.

(I) A medium was prepared containing 5% soya bean milk, 5% glucose. 2% yeast extract powder, 5% soya-bean peptone and water (pH=3). Culture fluid (80 ml) was added to each 100 g of rice and the mixture was sterilized in steam at 121° C. After cooling to a temperature below 40° C., the mixture was inoculated with *Monascus pilosus* Sato (AS 3.4646), and cultured at 30–34° C. for 3 days. The temperature was lowered to 23–25° C., and cultured for over 9 days. The mixture was sterilized in steam at 121° C. and then dried at 80° C.

(J) A medium was prepared containing 4% potato juice, 4% sugar, 3% yeast extract powder and water (pH=3). Silkworm chrysalis powder (5 g) and culture fluid (60 ml) were added to each 100 g of rice and the mixture was sterilized in steam at 121° C. After cooling to a temperature below 40° C. the mixture was inoculated with *Monascus fuliginosus* Sato (AS 3.569), and then cultured at 30–34° C. for 3 days. The temperature was lowered to 23–25° C. and culturing was continued for over 9 days. The mixture was sterilized in steam at 121° C. and dried under vacuum at 60–80° C.

(K) A medium was prepared containing 3% malt juice, 5% sugar, 6% thick beef juice and water (pH=3). Culture fluid (80 ml) was added to each 100 g of rice, and the mixture was sterilized in steam at 121° C. After cooling to a temperature below 40° C., the mixture was inoculated with *Monascus fuliginosus* Sato (AS 3.1098), and then cultured at 30–34° C. for 3 days. The temperature was lowered to 23–25° C. and culturing continued for over 9 days. The mixture was sterilized in steam at 121° C. and dried at a temperature of 80° C.

(L) The following procedures were used for large scale fermentation:

(1) Soaking the rice: Rice (500 kg) was placed in several layers of baskets. The chaff was cleaned in water, and the rice soaked in water for 16–24 hours. The rice was dredged from the water and dried (the content of water is approximately 22–24%).

(2) Steaming the rice: Dried rice was poured into a rice steamer and steamed for 50–70 minutes. The steamed rice was spread out on a bamboo mat or in baskets, dispersed, and cooled to a temperature below 40° C. The rice was then inoculated with approximately 20 kg of solid Monascus strain and 2.5–3 kg of acetic acid and stirred.

(3) Fermentation: For the first 3 days, the rice was turned over several times per day. The temperature was controlled between 30° C. and 34° C. After 3 days, the temperature was reduced to 23–25° C. The rice was turned over once daily, during which water (pH value adjusted to 3.5 using acetic acid) was added at quantity depending on the humidity of the fermenting mixture. The mixture was fermented for over 15 days.

(4) Preservation: After the fermentation process, the mixture was sterilized, dried and preserved.

The large-scale fermentation methods were used with all media and preparative processes described above by adding in the respective proportions of other ingredients. It should be noted that forced ventilation can be used in the fermentation process but that the return air must be sterile.

EXAMPLE 2

Pharmacology and Toxicology

Pharmacological and toxicological studies of the red rice of the present invention were performed in experimental animal models. Red rice was shown to dramatically decrease serum total cholesterol (TC) of endogenous hyperlipidemic rabbits, remarkably decrease TC and total triglyceride (TG) of exogenous hyperlipidemic rabbits, inhibit formation of arteriosclerosis plaque and lipid deposition in liver in hyperlipidemic rabbits, and decrease serum TC and TG of hyperlipidemic quails.

In acute toxicity studies, a LDS value cannot be determined. The highest tolerance dose of red rice in mice is over 16 g/kg, which is 533 times over the dose used in clinical treatment. Moreover, in other experiments, rats were continuously force-fed red rice for four months; no rats died or showed toxic symptoms due to this drug. Hematological indices, main viscera indices, blood biological indices, routine uroscopy and pathological examination did not show any differences between experimental groups and control groups.

EXAMPLE 3

Human Clinical Study I

The following two examples contain the methodologies and results of two human clinical trials that were carried out in China. The trials were designed to determine the efficacy of a red rice product in modulating circulating serum lipid and lipoprotein levels in humans, in resolving symptoms according to traditional Chinese medicine, and in establishing the safety of a red rice product.

In the first randomized human clinical trial, 446 patients with hyperlipidemia, who were also diagnosed as suffering from hypofunction and disorder of the spleen by traditional Chinese medicine, were divided into two treatment groups.

The first group (324 patients) received Xuezhikang capsules, which contained 0.3 g of a red rice product. The second group (122 patients) served as a control; they received Jiaogulan tablets containing a lipid-regulating drug (gynostemma pentaphyllum) that is based on traditional Chinese herbal medicine.

All the patients with primary hyperlipidemia stopped using serum lipid modulators two to four weeks prior to the beginning of the trial and received dietary advice. Serum samples was taken and laboratory tests was conducted to determine eligibility for the study. Only patients who met the following criteria were enrolled in the trial: total serum cholesterol (TC)>230 mg/dl (5.95 mmol/L) and triglyceride (TG)>200 mg/dl (>2.26 mmol/L). High density lipoprotein cholesterol (HDL-C) was also considered as a reference: male<40 mg/dl (1.04 mmol/L), female<45 mg/dl (1.16 mmol/L). All patients were diagnosed as deficient in the function of the spleen and having excess expectoration by traditional Chinese medicine. The patients also had the following symptoms: limb weakness; asthenic breathing; pain and oppressed feeling in chest; loss of appetite; distention and swelling on gastric region; whitish or purple dots on the tongue; thick-white or thick-slimy fur on the tongue; taut-slippery or hesitant-weak pulse.

Patients who had the following disorder or disease were excluded from the trial: myocardial infarction; cerebrovascular disease; severe wound or major surgery during the past half year; nephritic syndrome; hypothyroidism; acute and/or chronic hepatobiliary disorder; diabetes; gout; general allergic reactions; and psychosis.

The total number of patients enrolled was 446. In the group treated with red rice, there were 188 male and 126 female patients. The ratio of male versus female was 1.38:1 and the average age was 56.0±9 years old. There were 73 male and 45 female patients in the control group. The ratio of male versus female was 1.49:1 and average age was 56.4–9.1 years old. Between the two groups, there was no difference (P>0.05) found in baseline parameters including age, sex and course of disease, serum lipid and lipoprotein levels.

The group receiving red rice treatment took two Xuezhikang capsules orally, twice a day for 8 weeks. The control group took three Jiaogulan tablets twice a day for 8 weeks. All the patients maintained the same lifestyle and habits as before.

The following tests were performed at four and eight weeks: measurements of weight, blood pressure, and cardiac rhythm were performed. In addition, an electrocardiogram and routine physical examination was performed. The following parameters were monitored by laboratory tests: blood urea nitrogen (BLTN); creatinine; serum glutamic pyruvic transaminase (SGPT, ALT); serum glucose; and creatinine kinase (CK). To determine serum lipid and lipoprotein levels, a fasting (12 hours) venous blood sample was taken from patients who were told not to consume alcoholic beverages or food with a high fat content at the last meal prior to the tests. Serum obtained from the patients was separated immediately, and stored in $-20°$ C. for analysis. TC, TG and HDL-C were analyzed, and the LDL-C value was calculated according to the formula: LDL-C-TC-HDL-C—(TG/2.2).

Efficacy of treatment was evaluated according to the criteria set forth in "Clinical trial management: hyperlipidemia treatment using new Chinese materia medica" released by the Ministry of Health of China as follows:

1. Cure: All symptoms were eliminated or a reduction of the total symptom score by more than 90%, and a return of all laboratory test parameters to normal.

2. Effective: Symptoms were significantly relieved, i.e., symptom score reduced by 70%–89%. Serum lipid and lipoprotein did not reach normal, but were improved in one of the following respects: 1) reducing TC$\geq$20%; 2) reducing TG$\geq$40%; 3) reducing (TC-HDL-C)/HDL-C$\geq$20%; 4) increasing HDL-C>10 mg/dl.

3. Improvement: symptoms were relieved, i.e., symptom score reduced by 30%–69%. Serum lipid and lipoprotein levels were not normal but were improved in one of the following respects: 1) reducing TC at 10%–20%; 2) reducing TG$\geq$20% but <40%; 3) reducing (TC-HDL-C)/HDL-C$\geq$10% but <20%; 4) increasing HDL-C>4 mg/dl (0.14 mmol/L but <10 mg/dl.

4. Inefficacy: Symptom score was reduced by less than 30%, and the laboratory test parameters did not meet the criteria of effectiveness.

All the data are subjected to statistical analyses (the Student's t test, Chi-square test, Ridit assay for data of stratum, and U chart for percentiles analysis were used as appropriate).

TABLE 1

Efficacy comparison

| | Case number | Cure n | % | Effective n | % | Improvement n | % | Inefficacy n | % | Total Effective | | Improvement n | % |
|---|---|---|---|---|---|---|---|---|---|---|---|---|---|
| Treated Group | 324 | 169 | 52.2 | 89 | 27.5 | 44 | 13.5 | 22 | 6.8 | 258 | 79.7 | 302 | 93.2 |
| Control Group | 122 | 13 | 10.7 | 25 | 20.5 | 24 | 19.7 | 60 | 49.2 | 38 | 31.1 | 62 | 50.8 |

Ridit Analysis: u 10.04, p < 0.001

TABLE 2

Comparison of serum lipid and lipoprotein levels after treatment

| Parameter | Group | Case No. | Mean ± S Baseline mg/dl | Difference after 4 week difference in mg/dl | % Change | Difference after 8 week difference in mg/dl | % Change |
|---|---|---|---|---|---|---|---|
| TC | Treated | 251 | 273.5 ± 31.3 | −47.4 | −17.3** | −62.8 | −23** |
| | Control | 94 | 268.2 ± 25.4 | −13.2 | −4.9** | −18.9 | −7** |
| TG | Treated | 183 | 296.0 ± 75.5 | −66.3 | −22.4** | −108 | −36.5** |
| | Control | 72 | 289 ± 71.7 | −27.5 | −9.5* | −42.3 | −14.6** |
| HDL-C | Treated | 121 | 35.9 ± 4.4 | 4.2 | 11.8** | 7 | 19.6** |
| | Control | 55 | 35.1 ± 4.0 | 1.8 | 5* | 3 | 8.6** |
| LDL-C | Treated | 324 | 162.2 ± 52.4 | −36.5 | −22.5** | −46.3 | −28.5** |
| | Control | 122 | 157.3 ± 49.2 | −9 | −5.7** | −12.6 | −8** |
| TC-HDL-C/ HDL-C | Treated | 324 | 4.69 ± 1.44 | 1.3 | −22.7** | 01.6 | −34.2** |
| | Control | 122 | 4.79 ± 1.71 | 0.39 | −8.1** | −0.52 | −10.9** |

Note:
(+) indicates increase, (−) indicates decrease
*: p, 0.01, **: p < 0.001 vs. baseline
+: p < 0.05; ++: p < 0.01; +++: p < 0.001 vs. control Table 1 shows a comparison of overall efficacy. The score for the group which received red rice (treated group) was much higher than that in the control group (X'=9.7, P<0.001).

The percentage of patients in the treated group who reported the elimination of symptoms diagnosed by traditional Chinese medicine was much higher than that in the control group (p<0.05–0.001). Those symptoms were: condition of tongue (whitish or purple dots on the tongue; thick-slimy fur); pulse (slippery-taut or hesitant-weak); oppressed feeling in chest; loss of appetite; abdominal distention and swelling.

With respect to serum lipid and lipoprotein level, the efficacy scores for curing or reducing total serum cholesterol and total triglyceride level in the treated group were greater than that in the control group. The score for normalizing or increasing HDL-C, level and the score for reducing Atherosclerotic Index in the treated group were also much better than the control (P<0.001).

Table 2 indicates that both Xuezhikang-treated and control groups showed marked desirable changes in the levels of TC, TG, (TC-HDL-C)/HDL-C, HDL-C serum levels markedly. The effectiveness of Xuezhikang was found to be superior to that of Jiaogulan.

It was also observed that the higher the baseline of TC and TG in the serum, the more effective is the reduction of TC and TG after using Xuezhikang. As for HDL-C level, a greater increase was observed after treatment in patients who had a lower starting baseline.

TABLE 3

Effects of Xuezhikang capsule on patients with different abnormal levels serum lipid and lipoprotein.

| | TC (mg/g) | | | TG (mg/g) | | | HDL-C (mg/dl) | | |
|---|---|---|---|---|---|---|---|---|---|
| Parameter | <230 | 230–300 | >300 | <230 | 230–300 | >300 | >45 | 35–45 | <35 |
| Case No. | 73 | 206 | 45 | 141 | 112 | 71 | 161 | 114 | 49 |
| Mean baseline (mean) | 187.8 | 261.8 | 327.1 | 134.3 | 247.6 | 327.3 | 56.4 | 40.1 | 5.4 |
| Difference (4 weeks) | ↓20.5 | ↓42.5 | ↓69.8 | ↑2.7 | ↓51.4 | ↓89.8 | ↑1.3 | ↑4 | ↑5.4 |
| % changes | ↓10.9 | ↓16.2 | ↓21.3 | ↑2 | ↓20.8 | ↓24.1 | ↑2.3 | ↑10 | ↑17 |
| Difference (8 weeks) | ↓30.6 | ↓57.9 | ↓86.1 | ↓15.9 | ↓81.4 | ↓149.9 | ↑2.1 | ↑6.3 | ↑7.2 |

TABLE 3-continued

Effects of Xuezhikang capsule on patients with different abnormal levels serum lipid and lipoprotein.

| | TC (mg/g) | | | TG (mg/g) | | HDL-C (mg/dl) | | |
|---|---|---|---|---|---|---|---|---|
| % Changes | ↓16.3 | ↓22.1 | ↓26.3 | ↓11.8 | ↓32.9 | ↓40.2 | ↑3.7 | ↑15.7 | ↑22.8 |
| Comparison | | ** | ** | | ** | ** | | * | * |

(↑)indicates the value increase
(↓)indicates the value decrease
* P < 0.01; ** P < 0.001 vs baseline

TABLE 4

Effect of Xuezhikang capsule on apoA-I and apoB (mean ± S)

| Group | Case No. | Time Point | apoA-I | apoB | apoA-I/apoB |
|---|---|---|---|---|---|
| Treated Group | 88 | Baseline | 1.22 ± 0.19 | 1.2 ± 0.19 | 1.05 ± 0.25 |
| | | 4 Weeks | 1.32 ± 0.13(4) ↑8.2% | 1.09 ± 0.21(3) ↓9.2% | 1.25 ± 0.27(5) ↑19% |
| | | 8 Weeks | 1.28 ± 0.13 ↑4.9 | 0.99 ± 0.18(3) ↓18% | 1.33 ± 0.30(3) ↑26.7% |
| Comparison Group | 30 | Baseline | 1.19 ± 0.16 | 1.21 ± 0.15 | 1.00 ± 0.18 |
| | | 4 Weeks | 1.26 ± 0.11(1) ↑5.9% | 1.15 ± 0.17(1) ↓5% | 1.11 ± 0.14(2) ↑11.0% |
| | | 8 Weeks | 1.26 ± 0.09(1) ↑5.9% | 1.03 ± 0.15(3) ↓14.9% | 1.24 ± 0.21(3) ↑24.0% |

(1) P < 0.05; (2) P < 0.01; (3) P < 0.001; vs. baseline
(4) P < 0.05; (5) P < 0.05; vs. control Regarding the effect of Xuezikang on apolipoprotein as a-I (apoA-I) and apolipoprotein B (apoB), the serum levels of apoA-I in both groups were raised after therapy. Statistical results show a significant difference in apoA-I levels after a four week treatment. ApoB levels were reduced somaewhat in both groups, however, these reductions are not statistically significant. The treated group showed better improvement of apolipoprotein B and apoA-I/apoB over the control.

With respect to rheology, there were significant changes to in blood sedimentation and K-value in both groups after treatment (P<0.05–0.01). However, the treated group showed better results than the control group (P<0.05–0.01).

All 446 patients were subjected to the following laboratory tests before and after therapy: blood urea nitrogen (BUN); creatinine; serum glutamic pyruvic transaminase (SGPT, ALT); serum glucose; and creatinine kinase (CK); and routine examination of blood and urine. No clinically meaningful changes were found at the end of the trial.

Several patients developed a burning sensation in the stomach (six patients, 1.8%), experienced fullness in the stomach (three patients, 0.9%), and suffered dizziness (one patient 0.3%). All patients had previously finished the trial, and all the symptoms were spontaneously relieved without treatment. Two patients suffered gastritis after taking Xuezhikang and had to leave the trial. The results suggest that Xuezhikang is a safe and effective drug for lowering serum lipids and triglycerides.

In this trial, a lipid regulating agent known in traditional Chinese medicine was used as a positive control. The efficacy score in the Xuezhikang-treated group was much higher than that in the control group (P<0.001). Comparing the baseline, in Xuezhikang-treated group, serum level of high density lipoprotein cholesterol was elevated by 19.6% and total cholesterol, total triglyceride, low density lipoprotein cholesterol and Atherosclerosis Index were reduced by 23%, 36.5%. 28.5% and 34.2%, respectively. It was also observed that the higher the abnormality of the lipid and lipoprotein serum level, the more dramatic the modulation of lipid and lipoprotein levels can be achieved by Xuezhikang therapy. Xuezhikang can also reduce apolipoprotein B level, blood sedimentation and blood sedimentation K-value.

Overall, the results show that red rice was as a safe, effective agent for modulating serum lipid and lipoprotein levels. Red rice can also be used as a therapeutic agent for coronary artery disease and cerebrovascular disease caused by hyperlipidemia and/or athyrosis because red rice not only significantly reduced plasma TC, TG and Atherosclerosis Index, but also markedly raised plasma apolipoprotein in as a-I level.

EXAMPLE 4

Human Clinical Trial II

In this clinical trial, 84 patients with hyperlipidemia, and 56 patients who were also diagnosed with atherosclerosis were divided into two treatment groups: a group treated with Xuezhikang capsules and a control group treated with Jiaogulan tablets.

All patients were diagnosed as hyperlipidemic following the criteria set forth in "Clinical trial management: hyperlipidemia treatment using new Chinese materia medica" released by the Ministry of Health of China. After dietary advice for two to four weeks, blood samples were collected from patients with abnormal lipid and lipoprotein twice, two weeks prior to the trial. Only patients who met the following criteria were enrolled in the trial: total serum cholesterol (TC)>230 mg/dl (5.95 mmol/L) and triglyceride (TG)>200 mg/dl (>2.26 mmol/L). High density lipoprotein cholesterol (HDL-C) was also considered as a reference: male<40 mg/dl (1.04 mmol/L); female<45 mg/dl (1.16 mmol/L).

The symptoms included: limb tightness; asthenic breathing; pain and oppressed feeling in chest; loss of appetite;

distention and swelling of gastric region; whitish or purple dots on tongue; the thick-white or thick-slimy fur on tongue; taut-slippery or hesitant-weak pulse.

The severity of the symptoms as recognized by traditional Chinese Medicine were scored as follows:

| | | | Asthenic breathing |
|---|---|---|---|
| 0 | none | (−) | no asthenic breathing |
| 2 | light | (+) | having asthenic breathing with physical activity |
| 3 | moderate | (++) | having medium asthenic breathing with physical activity |
| 4 | severe | (+++) | having asthenic breathing at rest |

| | | | Limb tightness |
|---|---|---|---|
| 0 | none | (−) | no limb tightness |
| 2 | light | (+) | having limb tightness occasionally |
| 3 | moderate | (++) | having medium limb tightness very often |
| 4 | severe | (+++) | having severe limb tightness |

| | | | Chest tightness and pain |
|---|---|---|---|
| 0 | none | (−) | no chest tightness and pain |
| 2 | light | (+) | having chest tightness and pain occasionally |
| 3 | moderate | (++) | having medium chest tightness and pain very often |
| 4 | severe | (+++) | having severe chest tightness and pain at rest |

| | | | Loss of appetite |
|---|---|---|---|
| 0 | none | (−) | having normal appetite |
| 2 | light | (+) | losing appetite by ¼–⅓ |
| 3 | moderate | (++) | losing appetite by ⅓–½ |
| 4 | severe | (+++) | losing appetite more than ½ |

| | | | Abdominal distention and swelling |
|---|---|---|---|
| 0 | none | (−) | no this sign |
| 2 | light | (+) | having the sign occasionally |
| 3 | moderate | (++) | having this sign very often |
| 4 | severe | (+++) | having severe abdominal distention and swelling |

| | | Picture of the tongue | |
|---|---|---|---|
| | 0 | normal | (−) |
| | 1 | abnormal | (+) |

| | Pulse condition | |
|---|---|---|
| 0 | normal | (−) |
| 1 | abnormal | (+) |

| Symptom severity: | light: | score ≦12 |
|---|---|---|
| | moderate: | score 12–20 |
| | severe: | score >20 |

Patients diagnosed by traditional Chinese medicine according to the above symptoms, and patients with primary hyperlipidemia were enrolled.

The criteria for exclusion of patients were as follows:

a. myocardial infarction, cerebrovascular disease, severe wound or major surgery during last half year;

b. nephritic syndrome, hypothyroidism, acute and/or chronic hepatobiliary disorder, diabetes, gout;

c. familial hypercholesterolemia (monogenic-hypercholesterolemia);

d. secondary hyperlipidemia caused by other medication, for instance; phenothiazine, beta-adrenergic blocking agents, corticosteroid, oral contraceptive;

e. patients who used other lipid modulators during the last four weeks and patients using heparin or were on thyroidization;

f. pregnant and breast-feeding women;

g. patients with disorder of the other organs; and h. hylaxis syndrome, and psychosis.

The total number of patients enrolled was 116. There were 84 patients in the treated group and 32 patients in the control group. No difference of distribution in age, sex and course of disease were found between the two groups.

A randomized single-blind trial was conducted with two groups. The treated group (84 cases) took two Xuezhikang capsules (i.e., a red rice product of the present invention) twice a day. The control group (32 cases) took three Jiaogulan tablets (ShanXi factory of Chinese materia medica, lot number: 940730) twice a day. The course of treatment was eight weeks.

The measurements of serum lipid and lipoprotein levels and other scoring were performed prior to the therapy, and at four weeks and at eight weeks after therapy. The safety tests were conducted before and after therapy. A fasting venous blood sample was collected; patients were not allowed to consume alcohol or food with a high fat content in the last meal.

The following safety tests were conducted: blood and urea nitrogen (BUN); creatinine; serum glutaric pyruvic transaminase (SGPT, ALT); serum glucose; and creatinine kinase (CK). Total serum cholesterol (TC), total serum triglyceride (TG) and high density lipoprotein cholesterol levels were measured to determine efficacy. Other relevant clinical sign such as weight, high blood pressure, heart beat and rhythm, and hepatosplenopalpation were recorded.

Efficacy was evaluated according to the criteria set forth in "Clinical trial management: hyperlipidemia treatment using new Chinese materia medica" released by the Ministry of Health of China as follows:

1. Cure: All symptoms are eliminated or the total symptom score reduced by more than 90%; and every laboratory tested parameters reached normal levels.

2. Effective: Symptoms are significantly relieved, i.e., symptom score reduced by 70%–89%. Serum lipid and lipoprotein do not reach normal level but was improved in one of the following respects: 1) reducing TC≧20%; 2) reducing TG≧40%; 3) reducing (TC-HDL-C)-/HDL-C≧20%; 4) increasing HDL-C>10 mg/dl.
3. Improvement: Symptoms are relieved, i.e., symptom score reduced by 30%–69%. Serum lipid and lipoprotein did not reach normal levels but were improved in one of the following respects: 1) reducing TC at 10%–20%; 2) reducing TG≧20% but <40%; 3) reducing (TC-HDL-C)/HDL-C≧10% but <20%; 4) increasing HDL-C>4 mg/dl (0.14 mmol/L).
4. Inefficacy: Symptom score was reduced by less than 30% and laboratory test parameters did not meet the criteria of effectiveness.

All the data were subjected to statistical analysis. The student's t test, Chi-square test for counting data, and Ridit assay were used when appropriate.

Table 5 shows a comparison of the overall efficacy score of the two groups.

TABLE 5

| | | General Efficacy | | | |
|---|---|---|---|---|---|
| Group | Total Case Number | Cure | Effective | Improvement | Inefficacy |
| Treated | 84 | 39 | 25 | 13 | 7 |
| Control | 32 | 3 | 6 | 4 | 19 |

Ridit Analysis: u=5.18, P<0.01

Comparison: $X^2$=0.0 P>0.05

The total efficacy score in the treated group was much higher than that of the control group ($X^2$–22.95, P<0.01).

Table 6 shows a comparison of efficacies as defined by the standards of traditional Chinese medicine.

TABLE 6

| | Comparison of efficacy | | | | | | |
|---|---|---|---|---|---|---|---|
| | Red Rice | | | Control | | | |
| Symptoms | Before | After | Vanish % | Before | After | Vanish % | Statistics |
| Asthenic breathing | 35 | 15 | 57.1 | 12 | 6 | 50 | >0.05 |
| Limbs tight | 37 | 16 | 56.8 | 13 | 7 | 46.2 | >0.05 |
| Oppressed feeling in chest | 37 | 16 | 56.8 | 9 | 5 | 44.4 | * |
| Chest pain | 8 | 1 | 87.5 | 2 | 1 | 50 | * |
| Loss of appetite | 11 | 4 | 63.6 | 3 | 2 | 33.3 | * |
| Distension & swelling stomach | 31 | 11 | 64.5 | 7 | 6 | 14.3 | * |
| Pale tongue | 54 | 34 | 37 | 17 | 12 | 31.3 | >0.05 |
| Purple dot on tongue | 9 | 4 | 55.6 | 3 | 4 | 0 | * |
| Thick-whitish fur | 21 | 16 | 23.8 | 11 | 6 | 45.5 | >0.05 |
| Thick-slimy fur | 11 | 8 | 27.3 | 5 | 4 | 0 | |
| Slippery & string-like pulse | 28 | 22 | 21.4 | 13 | 8 | 33.3 | * |
| Weak-thread pulse | 24 | 16 | 33.3 | 8 | 3 | 62.6 | * |
| Slippery-fine pulse | 28 | 16 | 42.9 | 9 | 8 | 11.1 | * |

*P < 0.05 vs control

The percentage of patients who reported elimination of the symptoms as diagnosed by traditional Chinese medicine in the treated group was much higher than that in the control group (p<0.05), especially in the aspect of pain and oppressed feeling in chest, loosing appetite, distention and swelling on gastric region as well as purplish dots on the tongue.

The change in serum total cholesterol level is shown in Table 7.

TABLE 7

Change in serum total cholesterol level

| Group | Abnormal Case No. | Cure | Reduction >20% | Reduction 10–20% | Reduction <10% |
|---|---|---|---|---|---|
| Treated | 76 | 53 | 9 | 5 | 9 |
| Control | 28 | 4 | 0 | 2 | 22 |

Ridit Analysis: u=5.47 P>0.05
Efficacy ratio: $X^2$=39.96, P<0.001, vs. control

The scores for curing or reducing total serum cholesterol level in the treated group were greater than that in the control group.

The change in serum total triglyceride level is shown in Table 8.

TABLE 8

Change in serum total triglyceride level

| Group | Abnormal Case No. | Cure | Reduction >20% | Reduction 10–20% | Reduction <10% |
|---|---|---|---|---|---|
| Treated | 35 | 20 | 2 | 5 | 9 |
| Control | 13 | 6 | 2 | 1 | 4 |

Ridit Analysis: u=0.53 P>0.05
Efficacy ratio: $X^2$=0.007, P<0.05, vs. control

No significant difference in the scores for curing or reducing the serum total triglyceride level was observed between the two groups.

The change in high density lipoprotein-cholesterol level is shown in Table 9.

Table 10 shows the changes in Atherosclerotic Index which is the ratio of (TC-HDL-C)/HDL-C.

TABLE 10

Change of (TC-HDL-C)/HDL-C

| Group | Abnormal (>4) Case NO. | Cure >4 | Reduction >20% | Reduction 10–20% | Reduction <10% |
|---|---|---|---|---|---|
| Treated | 56 | 44 | 6 | 3 | 3 |
| Control | 14 | 3 | 1 | 2 | 8 |

Ridit Analysis: u=3.84 P>0.01

Efficacy ratio: $X^2$=23.41, P<0.01, vs. control

The data in Table 10 indicates that the both the Xuezhikang-treated and control groups improved HDLC serum levels markedly. The effectiveness of Xuezhikang was found to be superior to that of the control.

Table 11 shows the effect of Xuezhikang on regulating serum lipid and lipoprotein levels (X+/−S).

TABLE 11

Regulating Effect of Xuezhikang on serum lipid and lipoprotein (X ± S)

| Group | Time Point | Case No. | TC (mg/dl) | Case No. | TG (mg/dl) | Case No. | HDL-c (mg/dl) | Case No. | LDL-c (mg/dl) |
|---|---|---|---|---|---|---|---|---|---|
| Treated Group | Baseline | 76 | 273.9 ± 34.1 | 35 | 304.1 ± 86.8 | 24 | 35.3 ± 4.8 | 84 | 174.7 ± 48.1 |
| | 4 Weeks | | 253.9 ± 35.9 | | 270.3 ± 121.2* | | 39.5 ± 9** | | 141.4 + 477.6*** |
| | difference | | 35*** | | 33.8 | | 4.2# | | 33.3### |
| | | | ↓13.87% | | ↓11.11% | | ↑11.9% | | ↓19.1% |
| | 8 Weeks | | 216.7 ± 33.7 | | 206.5 ± 72*** | | 42.1 ± 7.6*** | | 126.8 + 39.6*** |
| | difference | | 57.3*** | | 97.6 | | 6.8 | | 49.9### |
| | | | ↓20.91% | | ↓32.09% | | ↑19.6% | | ↓27.4% |
| Control Group | Baseline | 28 | 265.4 ± 25 | 13 | 297.1 ± 72.1 | 10 | 35.3 ± 3.3 | 32 | 164.3 + 35.6 |
| | 4 Weeks | | 272.6 ± 33.3 | | 304.8 ± 0.141 | | 35.3 ± 3.7 | | 171.6 + 42.3 |
| | difference | | 7.2 | | 7.7 | | 0.02 | | 7.3 |
| | | | ↑2.7 | | ↑2.6% | | ↓0.06% | | ↑4.44% |
| | 8 Weeks | | 265 ± 35.8 | | 226.7 ± 88.1 | | 38.3 ± 7.3 | | 168 + 45.5 |
| | difference | | 0.5 | | 70.3 | | 2.98 | | 4.11 |
| | | | ↓0.2% | | ↓23.67% | | ↑8.43% | | ↑2.5% |

↑Increase *P < 0.001; P < 0.001; *P < 0.05 vs baseline
↓: Decrease ### P < 0.05) P < 0.05 vs. control

TABLE 9

Change in HDL-C levels.

| Group | Abnormal (>4) Case No. | Cure >4 | Reduction >20% | Reduction 10–20% | Reduction <10% |
|---|---|---|---|---|---|
| Treated | 24 | 11 | 1 | 3 | 9 |
| Control | 10 | 3 | 0 | 1 | 6 |

Ridit Analysis: u−1.03 P>0.05
Efficacy ratio: $X^2$=1.15, P<0.05, vs. control

A similar efficacy for normalizing or increasing HDL-C level was found in both groups.

Table 11 indicates that Xuezhikang improved TC, TG, (TC-HDL-C)/HDL-C, HDL-C serum levels markedly, but control group only improved TG significantly. Xuezhikang therapy was found to regulate TC, LDL-C more effectively than the control.

Table 12 shows the efficacy of Xuezhikang therapy on different baseline of serum lipid and lipoprotein.

TABLE 12

Efficacy comparison of Xuezhikang therapy on different baseline of serum lipid and lipoprotein.

|  | TC (mg/g) | | | TG (mg/g) | | | HDL-C (mg/dl) | | |
| --- | --- | --- | --- | --- | --- | --- | --- | --- | --- |
| Parameter | <230 | 230–300 | >300 | 230 | 230–300 | >300 | >45 | 35–45 | <35 |
| Case No. | 8 | 60 | 16 | 49 | 20 | 15 | 55 | 17 | 12 |
| Mean baseline (mean) | 192.01 | 261.8 | 327.1 | 134.3 | 247.6 | 327.3 | 56.4 | 40.1 | 5.4 |
| Mean (4 weeks) | 174.14 | 226.14 | 272.56 | 134.84 | 202.64 | 360.59 | 55.03 | 43.41 | 38.82 |
| % Changes | ↓9.31 | ↓12.621 | ↓17.62 | ↓4.05 | ↓16.2 | ↓6.87 | ↓2.68 | ↑7.49 | ↑24.05 |
| Mean (8 weeks) | 156.08 | 208.21 | ↓86.1 | 119.38 | 169.51 | 255.88 | 57.58 | 46.89 | 40.33 |
| % changes | ↓18.72 | ↓19.53 | ↓24.93 | ↓15.05 | ↓29.9 | ↓33.91 | ↑1.85 | ↑16.11 | ↑28.89 |
| Comparison |  | * | ** |  | ** | ** |  | ** | ** |

**P < 0.01; *P < 0.001 vs. control

The higher baseline of TC and TG in the serum, the more reduction is achieved after using Xuezhikang.

The results indicate that the score of cure, and the score of efficacy were 46.4% (38/84), 29.8% (25/84), respectively, in the Xuezhikang-treated (red rice treated) group and 9.4% (3/32), 18.8% (6/32) in the control group. Total efficacy ratio in the treated group (72%) was much higher than that in the control group (28.2%, P<0.001). There were significant differences between the two groups in terms of improving TC, LDL-C and (TC-HDL-C)/HDL-C.

No significant clinically meaningful change in the following parameters was observed during and after therapy: serum glutamic pyruvic transaminase (SGPT); blood and urea nitrogen (BUN); creatinine; serum glucose; cardioelectrogram; and routine examination of urine and blood. Three cases reported an increase in creatinine kinase (CK) (252, 260, 466 IU/L versus normal standard at 200 IU/L) in the treated group and one (256 IU/L) in the control group. No clinical symptoms were observed in any of these cases. The results show that a red rice product of the present invention is a safe and acceptable lipid-modulating agent.

Other Embodiments

It is to be understood that while the invention has been described in conjunction with the detailed description of thereof, the foregoing description is intended to illustrate and not limit the scope of the invention, which is defined by the scope of the appended claims. Other aspects, advantages, and modifications are within the scope of the following claims.

What is claimed:

1. A composition for treating elevated above normal serum cholesterol and/or triglycerides, said composition comprising:

a solid, impure residue separated from the fermentation broth of fermentation of the strain or mixtures of a strain of Monascus, said residue containing at least about 0.05% lovastatin by weight, and a pharmaceutically acceptable carrier, wherein said Monascus strain comprises a strain selected from the group consisting of *Monascus albidus* Sato AS 3.570, AS 3.4440, CGMCC No. 0317; *Monascus pilosus* Sato AS 3.4444, AS 3.4633, AS 3.4646, AS 3.4647; *Monascus pubigerus* Sato AS 3.4445, *Monascus ruber* van Tieghem AS 3.549, CGMCC No. 0315, CGMCC No. 0316; *Monascus paxii* Lingelsheim AS 3.4453; *Monascus fuliginosus* Sato AS 3.569, AS 3.1098, AS 3.2091, AS 3.2093, AS 3.2134, IFFI 05035, and *Monascus purpureus* Went CGMCC No. 0272.

2. The composition of claim 1, wherein said residue is the product of a process comprising:

culturing a lovastatin-producing Monascus strain in a culture medium comprising rice;

removing said culture medium to provide said solid residue;

optionally sterilizing said solid residue; and formulating said solid residue with said pharmaceutically acceptable carrier to provide said composition.

3. The composition of claim 1, wherein said residue is the product of a process comprising;

culturing a lovastatin-producing Monascus strain in a culture medium comprising rice;

removing said culture medium to provide a first solid residue;

optionally sterilizing said first solid residue;

extracting said first solid residue with alcohol to form an extract;

evaporating said alcohol and drying said extract to form a second solid residue;

optionally sterilizing said second solid residue; and formulating said second solid residue with said pharmaceutically acceptable carrier to provide said composition.

* * * * *